(12) United States Patent
Tanner

(10) Patent No.: US 6,217,597 B1
(45) Date of Patent: Apr. 17, 2001

(54) SURGICAL CUTTING DEVICE AND METHOD OF USING THE SAME

(75) Inventor: Howard Tanner, Logan, UT (US)

(73) Assignee: Eva Corporation, Bethesda, MD (US)

( * ) Notice: Subject to any disclaimer, the term of this patent is extended or adjusted under 35 U.S.C. 154(b) by 0 days.

(21) Appl. No.: 09/121,706

(22) Filed: Jul. 24, 1998

(51) Int. Cl.⁷ ................................................. A61B 17/32
(52) U.S. Cl. ............................ 606/167; 128/898; 606/225
(58) Field of Search ........................ 606/1, 159, 138, 606/167, 170, 171, 209, 224–233; 128/898

(56) References Cited

U.S. PATENT DOCUMENTS

| 4,562,596 | 1/1986 | Kornberg . | |
| 4,787,899 | 11/1988 | Lazarus . | |
| 5,042,707 | 8/1991 | Taheri . | |
| 5,676,696 | 10/1997 | Marcade . | |
| 5,759,150 | * 6/1998 | Konou et al. | 606/159 |
| 5,899,912 | * 5/1999 | Eaves | 606/159 |
| 5,904,679 | * 5/1999 | Clayman | 606/159 |
| 5,910,150 | * 6/1999 | Saadat | 606/159 |

* cited by examiner

Primary Examiner—Glenn K. Dawson

(57) ABSTRACT

The present invention is directed to a surgical cutting device. The surgical cutting device may include a housing, an assembly for securing the cutting device upon an object to be cut, and a cutting assembly for cutting the object. The cutting device permits the close cutting of control lines, sutures or other surgical components during a surgical procedure.

4 Claims, 5 Drawing Sheets

SURGICAL CUTTING DEVICE AND METHOD OF USING THE SAME

FIELD OF THE INVENTION

The present invention relates generally to a cutting device. In particular, the present invention is directed to a surgical cutting device for use in remote controlled surgical procedures. The present invention is also directed to a method of operating the cutting device.

BACKGROUND OF THE INVENTION

Recent developments in the repair of abdominal aortic aneurysms permit minimally invasive surgical procedures through either an axillary or brachial incision or both. This requires the remote manipulation of a repair graft and surgical components. The proximal repair graft is positioned and manoeuvred within the vessel through the use of control lines that are attached to the perimeter of the graft lip and extend to the axillary/brachial incision. Upon completion of the repair procedure, it is necessary to remove the control lines from the vessel. Furthermore, it is desirable to remove as much of the control line as possible to prevent the buildup of thrombus on the remnant control line. There are currently no prior art devices available that are capable of closely cropping these control lines to prevent the referenced build-up.

OBJECTS OF THE INVENTION

It is therefore an object of the present invention to provide a cutting device for use in surgical procedures.

It is another object of the present invention to provide a cutting device that may be used in remote controlled surgical procedures.

It is another object of the present invention to provide a cutting device that may be used in intraluminal surgical procedures.

It is another object of the present invention to provide a cutting device that may be used in minimally invasive surgical procedures.

It is another object of the present invention to provide a cutting device that is capable of cutting control lines.

It is another object of the present invention to provide a cutting device that is capable of cutting suture material.

It is another object of the present invention to provide a method of cutting control lines.

It is another object of the present invention to provide a method of removing a control line during a remote controlled surgical procedure.

It is another object of the present invention to provide a method of removing suture material during a remote controlled surgical procedure.

It is another object of the present invention to provide a cutting method using a thermoelectric device.

It is another object of the present invention to minimize remnant line upon which thrombus can form.

It is another object of the present invention to provide a cutting device that permits close cropping of control lines to prevent thrombus build-up.

SUMMARY OF THE INVENTION

The present invention is directed to a surgical cutting device. The surgical cutting device may include a housing, an assembly for gripping the cutting device upon the object to be cut, and cutting assembly for cutting the object. The housing may be formed from a flexible material. The assembly for gripping the cutting device may be positioned within the housing. Furthermore, the cutting assembly may be positioned within the housing.

The present invention further includes an assembly for remotely actuating the cutting assembly. The actuating assembly may include electronic circuitry that delivers an electric current to the electrothermal cutting assembly or filament. The electrothermal cutting device includes at least one filament. The gripping assembly may include a gripping mechanism for gripping the control line. The securing assembly preferably engages the control line or suture within the housing.

The present invention is also directed to a method of cutting a control line or suture located within a vessel. The method includes the steps of releasably securing a cutting device to the control line, positioning the cutting device within the vessel at a desired location, and operating the cutting device to cut the control line within the vessel. The method may further includes the step of removing the cutting device from the vessel.

The step of releasably securing the cutting device to the control line may include the step of positioning a housing of the cutting device around a portion of the control line. Additionally, the step of operating the cutting device may include the step of applying focused heat to the control line.

It is to be understood that both the foregoing general description and the following detailed description are exemplary and explanatory only, and are not restrictive of the invention, as claimed. The accompanying drawings, which are incorporated herein by reference, and which constitute a part of this specification, illustrate certain embodiments of the invention, and together with the detailed description serve to explain the principles of the present invention.

BRIEF DESCRIPTION OF THE DRAWINGS

The invention will be described in conjunction with the following drawings in which like reference numerals designate like elements and wherein.

DETAILED DESCRIPTION OF PREFERRED EMBODIMENTS

Figure 1:
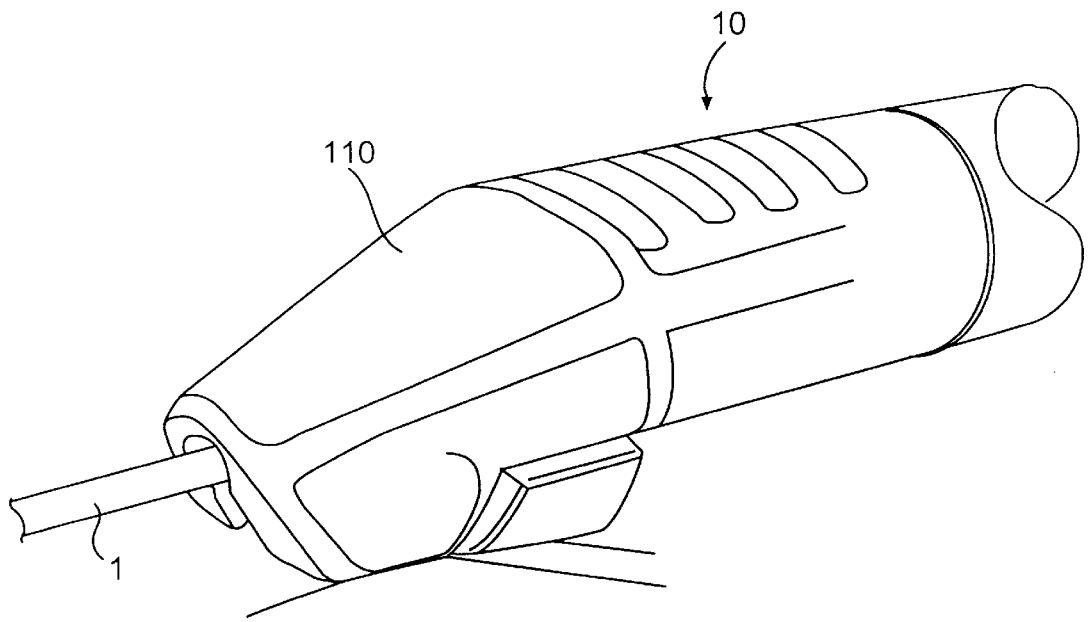
FIG. 1 is a perspective view of a cutting device according to the present invention.
Figure 2:
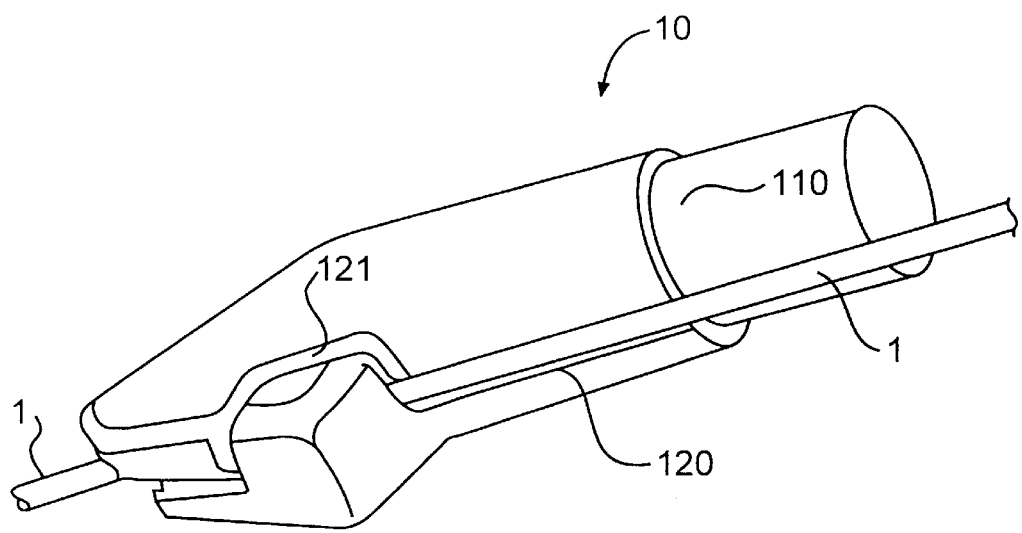
FIG. 2 is another perspective view of the cutting device of FIG. 1.

FIG. 1 depicts a surgical cutting device 10 according to an embodiment of the present invention. The cutting device 10 includes a housing 110. The housing 110 may be flexible. Furthermore, the housing 110 may be formed from a polymeric material. The housing 110 preferably includes a slot 120 located therein, as shown in FIG. 2. The slot 120 permits the securement of the cutting device 10 to a control line 1.

The housing 110 may have an angled exterior, as shown in FIG. 1, to facilitate the advancement of the cutting device 10 within a vessel, not shown. The housing 110 preferably includes a hollow interior 111, as shown in FIG. 2. At least one roller assembly 130 is located within the hollow interior 111. The at least one roller assembly 130 permits the advancement of the cutting device 10 along the control line 1. The at least one roller assembly 130 may be rotatably mounted in the housing 110 within the hollow interior 111.

Figure 4:
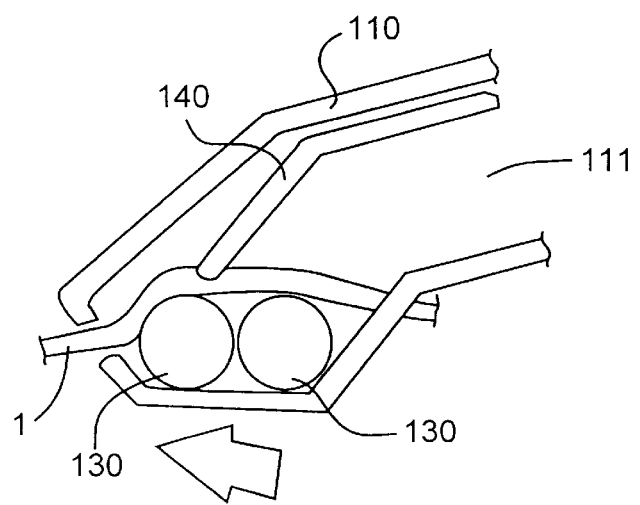
FIG. 4 is a side view of a cutting assembly of the cutting device of FIG. 1.
Figure 3:
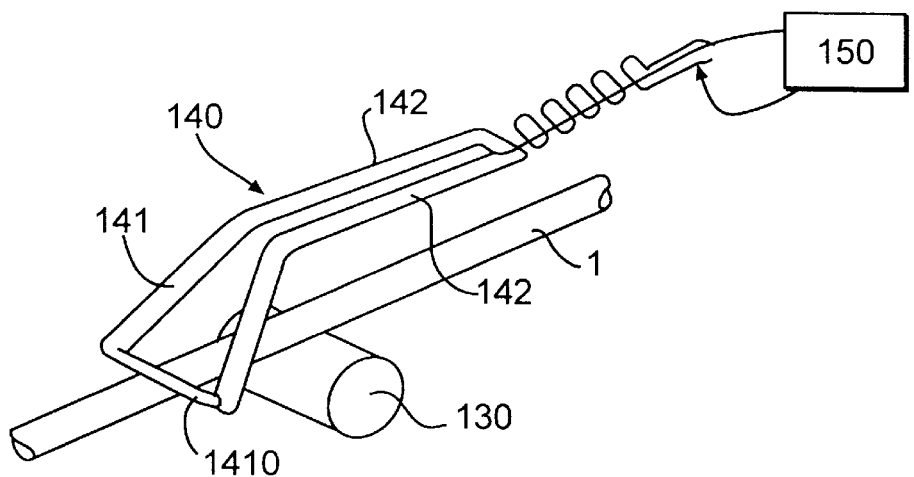
FIG. 3 is a schematic view of a cutting assembly of the cutting device of FIG. 1.

A cutting assembly 140 is also positioned with the hollow interior 111 of the housing 110. The cutting assembly 140 is preferably a thermoelectric operated cutting device, as shown in FIGS. 3 and 4. The thermoelectric cutting device 140 preferably includes an insulated tungsten filament 141 having an exposed portion 1410. The present invention is not limited to tungsten rather ni-chrome, inconel, etc. may be used. A portion of the filament 141 are insulated. The insulated portions 142 are preferably formed from a suitable heat and electrically insulating material. Remotely controlled electronics 150 provide power via traces to the filament 141. The low resistivity power traces conduct electricity to the higher resistivity filament 141. The filament is heated and in turn performs the cutting operation to sever the control line 1 or other suitable surgical component.

It is contemplated that the present invention is not limited to the above-described cutting assembly 140, rather other cutting assemblies are contemplated to be within the scope of the present invention. For example, an electrocautery based device may be used.

The cutting operation will now be described using the above-described cutting device 10. The cutting operation will be described in connection with the repair of an abdominal aortic aneurysm. It, however, is contemplated by the inventor of the present invention that the cutting device 10 may be used in other intraluminal remotely controlled surgeries where minimal invasion is desired.

During the repair of an abdominal aortic aneurysm, a repair graft is inserted into the vessel to repair the diseased portion of the vessel. Control lines 1 are used to align and manoeuvre the repair graft within an infra, juxta or renal positioning. The control lines 1 are radially positioned about the perimeter of the proximal lip of the graft and extend cephalad to the axillary orbrachial incision and thereafter to a hand controller, not shown. Once the graft has been secured in place, it is desirable to remove the control lines 1. Furthermore, it is desirable to remove the control lines 1 from the repair graft and the vessel with minimal impact upon graft/vessel connection. The graft/vessel connection may possibly experience damage such as separation or tearing if the entire control line is removed by pulling the control line 1 from the vessel in a single direction. The present invention permits removal of the control line 1 from the vessel and minimizes detrimental impact on the graft/vessel connection.

The cutting device 10 is placed on the control line 1 by inserting the control line into the slot 120 of the housing 110. The angled portion 121 of slot 120 permits the control line 1 to be aligned within the housing 110 such that the control line 1 is located between the at least one roller assembly 130 and the cutting assembly 140. The cutting device 10 is then fed through the vessel over the control line 1 to a position adjacent the repair graft. The arrangement of the slot 120, the cutting assembly 140 and the at least one roller assembly 130 permits the cutting device 10 to be advanced over the control line 1 through, for example, the axillary incision to the transition point of the repair graft and the control line 1, while restricting the removal of cutting device 10. The filament 141 and the at least one roller assembly 130 engage the control line 1 such that it is difficult to pull the cutting device 10 in a reverse direction prior to cutting the control line 1.

Once the cutting device 10 is positioned at the above-described transition point, the cutting assembly 140 is activated by turning on the control electronics "CE" 150. The CE 150 conducts power via the exposed filament 141 to heat the exposed portion 1410. The heated filament 141 then cuts through the control line 1. The control line 1 and the cutting device 10 are then easily removed from the vessel. The above-described process is then repeated sequentially until all of the control lines 1 are removed from the vessel.

The cutting device 10 according to the present invention permits the close-cropping of the control line 1 with respect to the graft. This prevents the buildup of thrombus at the graft/vessel interface.

The operation of the cutting device 10 has been described in connection with the removal of control lines 1 during a surgical procedure. However, it is contemplated that the present invention is capable of being used in other applications including but not limited to suture cutting. The present invention is capable of cutting various surgical materials which include Prolene™, Gore-Tex™ and Collagen.

Figure 5:
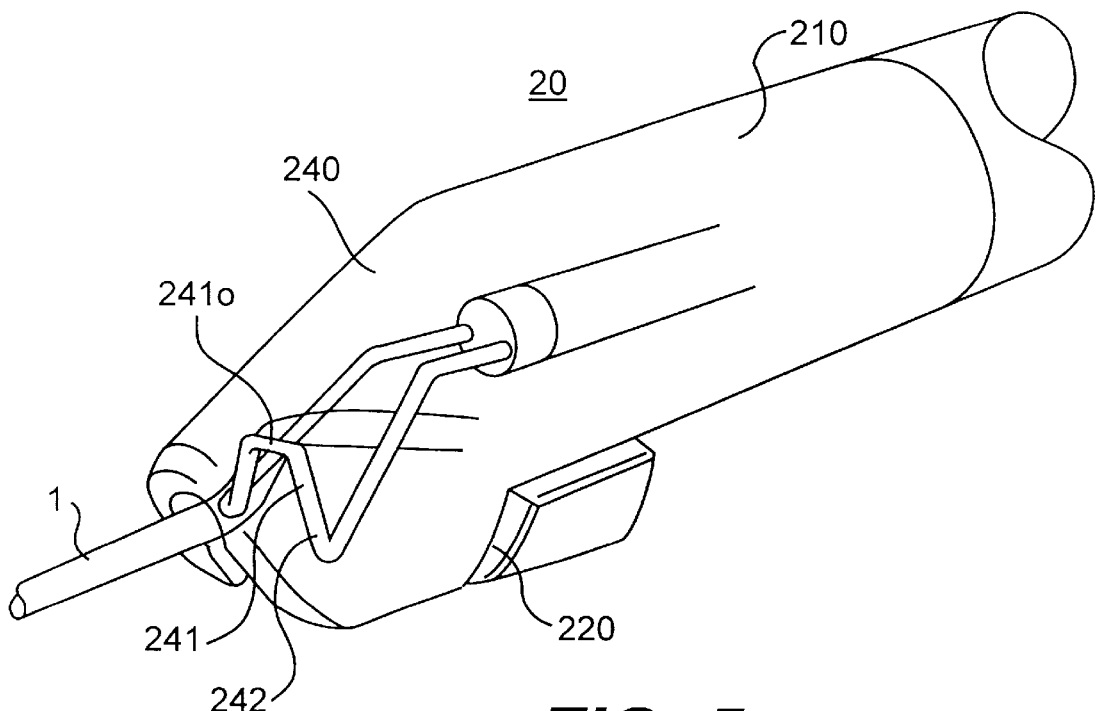
FIG. 5 is a perspective view of a cutting device according to another embodiment of the present invention.
Figure 6:
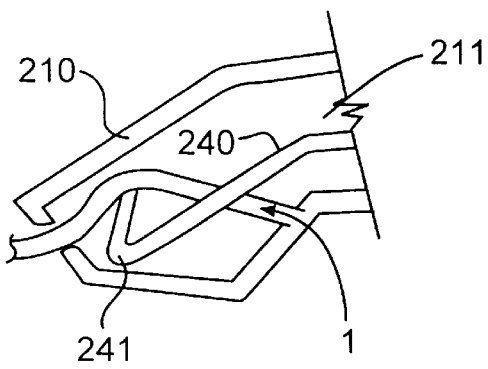
FIG. 6 is a schematic view of a cutting assembly of the cutting device of FIG. 5.

Another embodiment of the cutting device 20 is illustrated in FIG. 5 and FIG. 6. The cutting device 20 includes a housing 210. The housing 210 may be flexible. Furthermore, the housing 210 may be formed from a polymeric material. The housing 210 preferably incorporates a slot 220 located therein, as shown in FIG. 5. The slot 220 permits the securement of the cutting device 20 to a control line 1.

As discussed above in connection with the cutting device 10, the housing 210 may also have an angled exterior to facilitate the advancement of the cutting device 20 within the vessel. The housing 210 preferably includes a hollow interior 211, as shown in FIG. 6. The cutting device 20 differs from the cutting device 10 in that the at least one roller assembly 130 has been eliminated. In this arrangement, the control line 1 is placed over the filament 241 of the cutting assembly 240, as shown in FIG. 6.

The cutting assembly 240 is positioned within the hollow interior 211 of the housing 210. The cutting assembly 240 is preferably a thermoelectric device. The thermoelectric cutting device 240 preferably includes a filament 241 of tungsten ni-chrome, inconel, etc. having an exposed portion 2410. Portions of the tungsten filament 241 are insulated. The insulated portions 242 are preferably formed from a suitable heat and electrically insulating material. The cutting device 240 is also powered by remote control electronics 150, as shown in FIG. 3 discussed above. The "CE" provide power to the filament 241. The power traces conduct electricity to the filament 241 which having higher electrical resistivity than the copper traces, heats thereby enabling the cutting operation that severs the control line 1 or other suitable surgical component.

The cutting device 20 operates in a similar manner to the cutting device 10. The arrangement of the filament 241 engages the control line 1 such that it is difficult to pull the cutting device 20 in the converse direction prior to cutting the control line 1.

Figure 7:
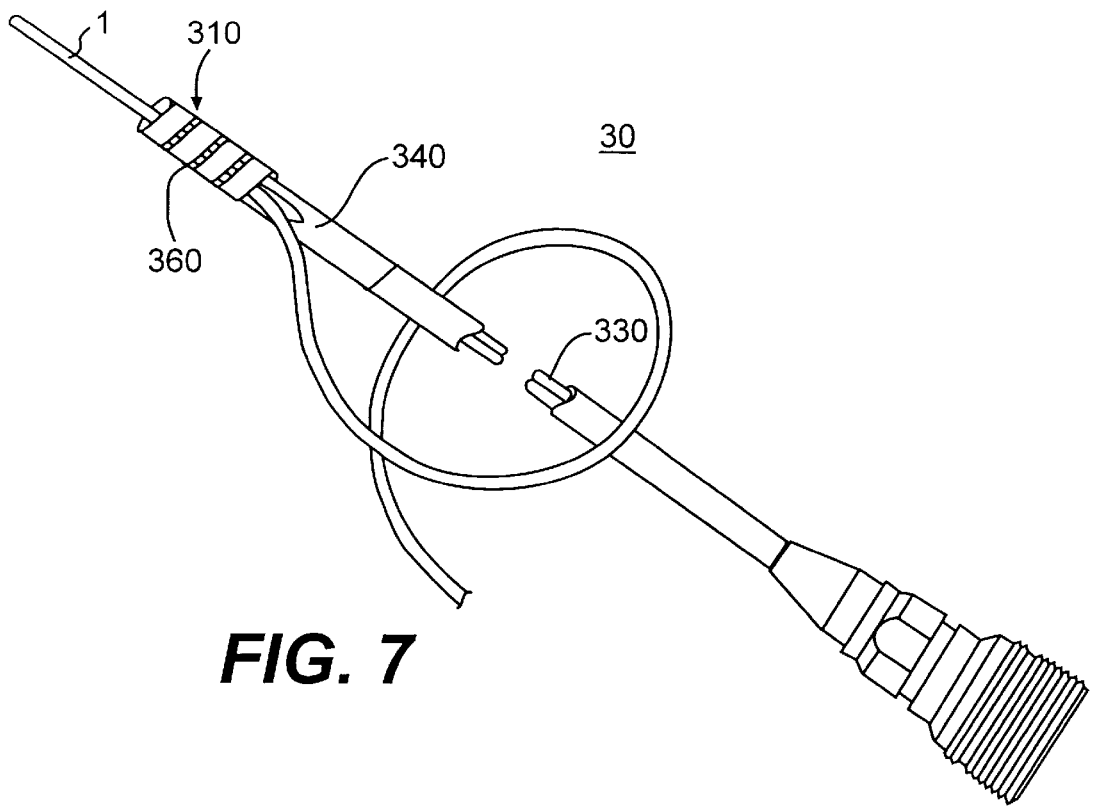
FIG. 7 is a schematic view of a cutting device according to another embodiment of the present invention.
Figure 9:
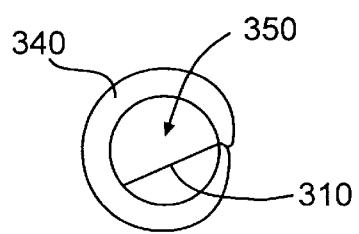
FIG. 9 is an end view of the cutting device of FIG. 7.
Figure 8:
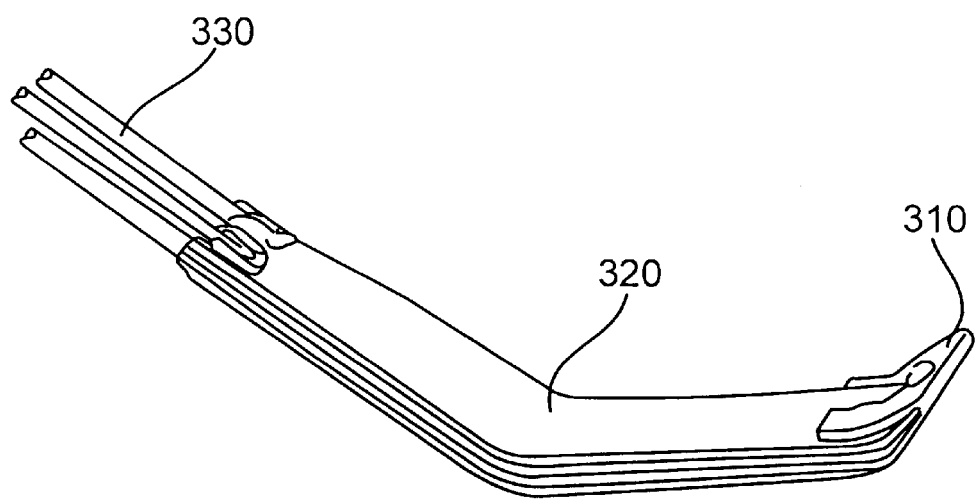
FIG. 8 is a schematic view of the components of the cutting device of FIG. 7.
Figure 10:
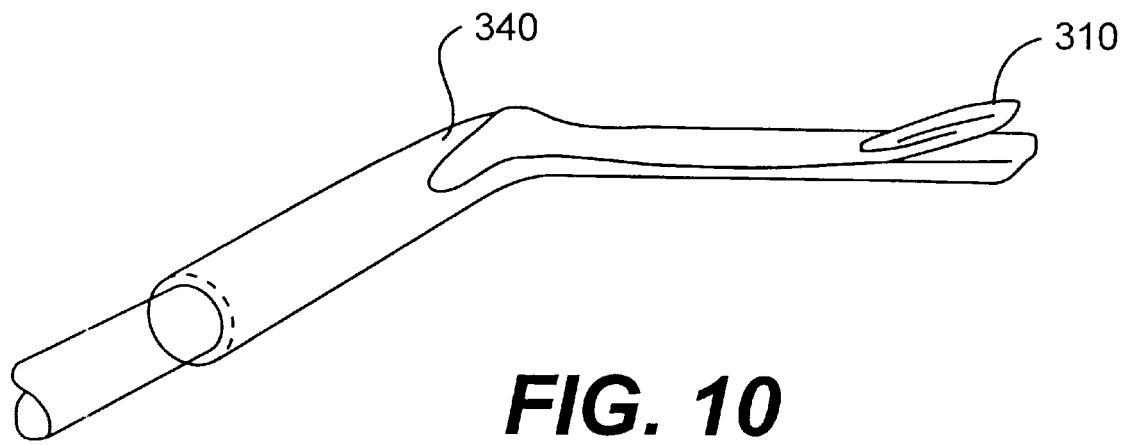
FIG. 10 is a schematic view of the cutting device of FIG. 7 in an unwound configuration.

Another embodiment of the cutting device 30 is illustrated in FIGS. 7–9. The cutting device 30 includes a cutting assembly 310. The cutting assembly 310 preferably includes a thermoelectric device. The thermoelectric device preferably includes a tungsten, ni-chrome, inconel, etc. filament. The cutting assembly 310 is secured to a doublesided flexible circuit 320. The flexible circuit 320 is connected to at least two electrical conductors 330. The at least two electrical conductors 330 supply electrical current to the flexible circuit 320 which delivers power via traces to the cutting device 310. The flexible circuit 320, the at least two electrical conductors 330 and a portion of the cutting assembly 310 are insert molded within housing 340.

In a preferred embodiment, the flexible circuit 320 and the cutting assembly 310 contained within the housing 340 are coiled coaxially with respect to cable 330, as shown in FIG. 7. In this orientation, a free end of the cutting assembly 310 projects into a central opening 350 of the housing 340, as shown in FIG. 9.

It is contemplated that the present invention is not limited to a flexible circuit 320; rather, the flexible circuit may be omitted. In this arrangement, the filament is directly attached to the power traces.

The cutting operation will now be described using the above-described cutting device 30. The cutting device 30 is placed on the control line 1 by inserting the control line 1 within the slot 360 created by the coiling of the housing 340 such that the control line 1 is located within the central opening 350. The control line 1 is in contact with the cutting assembly 310. The control line 1 is cut by sending power via the control electronics through the flexible circuit 320 to the filament 310. This in turn heats the cutting device 310 to cut the control line 1. The "CE" 150, discussed above provide power to the cutting assembly 310. The power traces conduct electricity to the cutting assembly 310 which having higher electrical resistivity than the copper traces, heats thereby enabling the cutting operation that severs the control line 1 or other suitable surgical component.

It will be apparent to those skilled in the arts that various modifications and variations can be made in the construction and configuration of the present invention, without departing from the scope or spirit of the invention. It is intended that the present invention cover the modifications and variations of the invention, provided they come within the scope of the appended claims and their equivalence.

What is claimed is:

1. A method of cutting a control line located within a vessel during a surgical procedure, said method comprising the steps of:

releasably securing a cutting device to the control line outside of the vessel;

advancing the cutting device along the control line within the vessel;

positioning the cutting device within the vessel at a desired location; and operating the cutting device to cut the control line at the desired location within the vessel.

2. The method according to claim 1, further comprising the step of:

removing the cutting device from the vessel after the step of operating the cutting device to cut the control line.

3. The method according to claim 1, wherein said step of releasably securing the cutting device to the control line includes the step of positioning a housing of the cutting device around a portion of the control line.

4. The method according to claim 1, wherein said step of cutting incorporates the application of thermoelectrically generated heat to the control line.

* * * * *